United States Patent [19]

Allcock et al.

[11] 4,239,755
[45] Dec. 16, 1980

[54] STEROIDAL CYCLOTRIPHOSPHAZENES

[75] Inventors: Harry R. Allcock; Timothy J. Fuller; Kiyotoshi Matsumura, all of State College, Pa.

[73] Assignee: The United States of America as represented by the Department of Health, Education and Welfare, Washington, D.C.

[21] Appl. No.: 52,728

[22] Filed: Jun. 28, 1979

[51] Int. Cl.³ .................. A01N 9/36; A61K 31/66; C07J 43/00
[52] U.S. Cl. .................. 424/209; 260/239.5
[58] Field of Search .................. 260/239.5; 424/209

[56] References Cited

U.S. PATENT DOCUMENTS

| | | | |
|---|---|---|---|
| 3,496,167 | 2/1970 | Morrow | 260/239.5 |
| 3,887,699 | 6/1975 | Yolles | 424/19 |
| 4,003,990 | 1/1977 | Jacquet et al. | 424/43 |
| 4,027,009 | 5/1977 | Grier et al. | 424/78 |

Primary Examiner—Elbert L. Roberts
Attorney, Agent, or Firm—John S. Roberts, Jr.

[57] ABSTRACT

Steroidal cyclotriphosphazenes of the formula

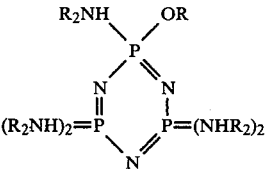

wherein R is the residue of a 3- or 17-hydroxysteroid and $R_2$ is alkyl, are hydrolytically labile compounds adapted for slow release in vivo of active steroidal compounds of the formula ROH.

9 Claims, No Drawings

STEROIDAL CYCLOTRIPHOSPHAZENES

The invention described herein was made in the course of work under a grant or award from the Department of Health, Education and Welfare.

TECHNICAL FIELD

This invention relates to novel 3- or 17-cyclotriphosphazene derivatives of steroids, which can slowly hydrolyze to release 3- to 17-hydroxy steroids.

PRIOR ART STATEMENT

Morrow (U.S. Pat. No. 3,496,167) discloses that estratriene 3-(1-phenyl-1H-tetrazol-5-yl) ethers are produced by reaction between a 5-halo-1-phenyltetrazole compound and a 3-hydroxyestratriene and that the products have estrogenic and antifertility activity.

Grier et al (U.S. Pat. No. 4,027,009) relates to the use of non-biodegradable linear quaternary poly[(alkylimino)-alkylene] polymers as a bindant for bile acids such as cholesterol.

Jacquet et al (U.S. Pat. No. 4,003,990) discloses attachment of anti-inflammatory residues having a carboxylic acid function to a vinylic polymer chain by means of an intermediate covalent function. The product permits sustained release of the active drug material.

The following disclose incorporation of a drug into a biodegradable polyester composition:
U.S. Pat. Nos. 3,887,699, Yolles; 3,983,209, Schmitt; 4,130,639, Shalaby et al.

The use of water-soluble poly(organophosphazenes), e.g., $[NP(NHCH_3)_2]_n$ as carriers for coordinatively bonded Pt anti-cancer drugs has been investigated by R. W. Allen et al, *J.Am.Chem.Soc.*, vol. 99, 3987 (1977) and H. R. Allcock et al, ibid, 3984 (1977).

"The Reaction of Steroid Salts with Hexachlorocyclotriphosphazene" and conversion to $N_3P_3(NHCH_3)_5OR$, wherein R is a residue of a 3- or 17-hydroxy steroid, as a prototype for the synthesis of related biodegradable high polymers, was reported by H. R. Allcock et al in a paper presented in September 1978, at the National Meeting of the American Chemical Society and is incorporated herein by reference.

DISCLOSURE OF INVENTION

This invention relates, in a compositional aspect, to a hydrolytically labile compound of the formula

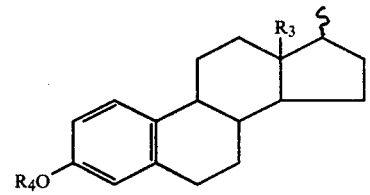

wherein $R_1$ is

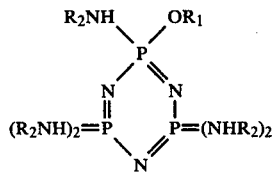

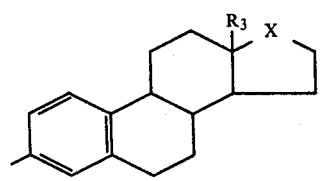

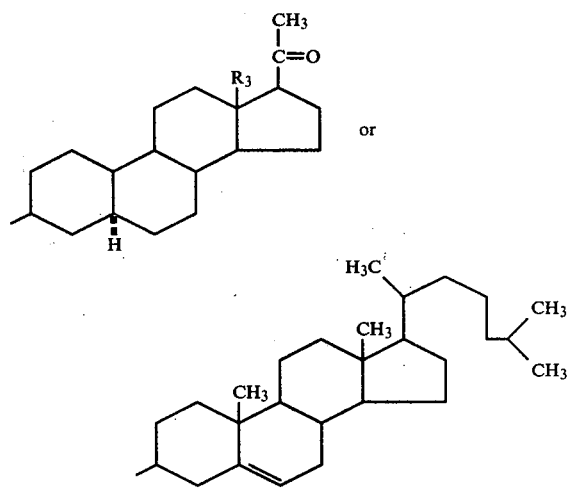

and $R_2$ is alkyl of 1–4 carbon atoms; $R_3$ is alkyl of 1–2 carbon atoms; $R_4$ is alkyl of 1–4 carbon atoms and X is $CH_2$, $C=O$,

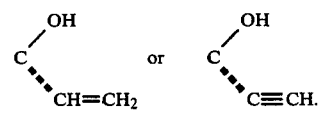

In another compositional aspect, this invention relates to a slow release steroidal medicament, comprising a hydrolytically labile compound as above, in admixture with a pharmaceutically acceptable carrier.

The products of the invention can be prepared from hexachlorocyclotriphazene by the equations:

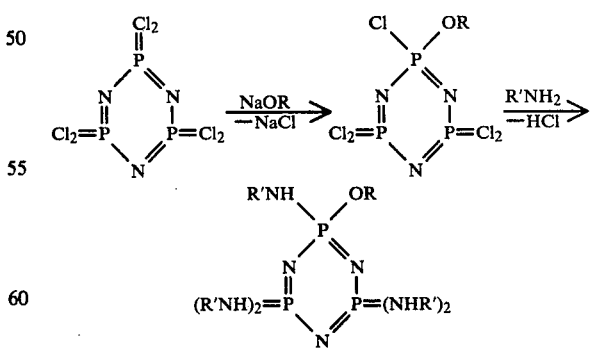

wherein R is a residue of a 3- or 17- hydroxysteroid and R' is alkyl.

Polymeric carrier molecules for steroids for use in birth control or chemotherapy can be obtained from the cyclic trimer as follows:

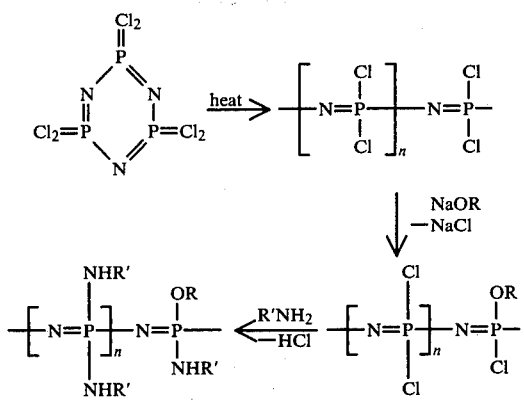

It is contemplated that R' can also be H, $CH_2COOC_2H_5$, imidazolyl and $NH_2$ as well as alkyl, and that n can be 85–95% of the polymeric —N=PCl$_2$— units. It will be appreciated that phosphazene polymers can be designed to degrade hydrolytically to phosphate, which is an essential mineral; and to ammonia, which is a harmless, readily excretable compound or to an amine or amino acid.

BEST MODE OF CARRYING OUT THE INVENTION

The 3- or 17-hydroxy steroids were converted to sodium salts by treatment with sodium hydride either at room temperature or in boiling tetrahydrofuran.

Some steroids, such as estrone, pregnenolone and mestranol contain additional groups which could react with sodium hydride. Accordingly, care was taken to limit the reaction to that of the hydroxyl group. For example, estrone was allowed to react with sodium hydride under mild conditions in very dilute solution to avoid self-condensation reactions of the 17-carbonyl group.

Treatment of excess $(NPCl_2)_3$ with dilute solutions of the sodium salts of desoxoestrone, estrone or estradiol 3-methyl ether resulted in the formation of corresponding mono-steroidal substituted phosphazenes. Sodium chloride was precipitated and identified by X-ray powder diffraction analysis. The more acidic steroidal alcohols, e.g., desoxoestrone and estrone gave higher yields of steroidal phosphazene. This result was attributed to the relatively higher efficiency of steroidal salt formation, rather than to direct steric effects. Preferably, these reactions are carried out with dilute solutions of the reactants at about 25° C. When more concentrated solutions and higher temperatures ($\approx$70° C.) were employed, side reactions became serious.

Owing to their hydrolytic instability, the steroidal phosphazenes of the formula $N_3P_3Cl_5(OR)$ derived from desoxoestrone, estrone and estradiol-3-methyl ether were not isolated in an ultra-pure state, but were characterized in solution by $^{31}P$ and $^{13}C$ nmr, infrared, or electronic spectral techniques, and were used directly for conversion to the P-aminophosphazenes.

Very low yields of $N_3P_3Cl_5(OR)$ were obtained (<5%) when the sodium alkoxide salts from pregnenolone or cholesterol were allowed to react with $(NPCl_2)_3$. The low yields are not attributed to low reactivity of the nucleophiles because $^{31}P$ nmr spectra showed that 17% of the $(NPCl_2)_3$ had reacted with the sodium salt of pregnenolone and 23% of the $(NPCl_2)_3$ had reacted with the salt formed from cholesterol. The main side reaction appeared to be a dehydration process similar to that reported by R. J. W. Cremlyn et al, *Phosphorus*, vol. 6, 201 (1976) during the reaction of cholesterol with phosphorus oxychloride. The mechanism of this dehydration probably involves the intermediate formation of, a cholesteryl cyclotriphosphazene followed by loss of the phosphazene as a leaving group by an $S_N1$ mechanism. This step could be encouraged by anchimeric assistance by the $\pi$-electrons of the 5,6-double bond to yield a stabilized cation:

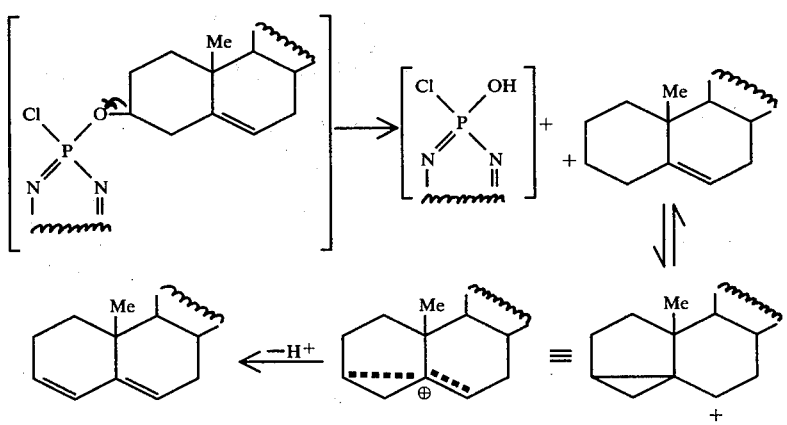

Two different procedures were used to produce salts at the 17-position of mestranol without reaction of the acetylenic unit. In the first, reaction of mestranol with excess sodium hydride, removal of excess sodium hydride, and addition of a stoichiometric equivalent of mestranol to the reaction mixture assured the absence of the acetylide salt. In the second, addition of a stoichiometric amount of methyllithium to mestranol gave the lithium alcoholate.

Mass spectrometric analysis of the reaction products formed from the cholesteryl salt revealed the presence of a $C_{27}H_{44}$ ion at m/e=368, which was assigned to the ion from 3,5-cholestadiene.

Sodium and lithium alkoxide salts at the 17-position of mestranol did not react with $(NPCl_2)_3$ at 25° C. in tetrahydrofuran; at elevated temperatures (70° C.), the tertiary alkoxide or alcohol was dehydrated. A similar reaction occurred with estradiol-3-methyl ether at 70° C. Side reactions also occurred when estrone-3-methyl ether was treated with $(NPCl_2)_3$. No reaction was evident in tetrahydrofuran at 25° C., but at higher temperatures hydrogen chloride was evolved. Because dry cyclohexanone behaved similarly, it is thought that the reaction involved the carbonyl group at position 17 in estrone 3-methyl ether. However, the reaction with cyclohexanone was complex.

The preferred intermediates of the formula $N_3P_3Cl_5(OR)$ are therefore those wherein OR is derived from an aromatic hydroxyl in the A ring of a steroidal compound or a secondary steroidal hydroxyl, of which desoxoestrone, estrone, pregnenolone, estradio 3-methyl ether and cholesterol are exemplary, rather than limiting.

Methylamine is exemplary of nucleophiles which can be used to replace the remaining halogen atoms in $N_3P_3Cl_5(OR)$. The resulting methylamino residue is a water-solubilizing side group for cyclo- or polyphosphazenes and the small steric size of methylamine would be expected to provide a maximum impetus for total displacement of the remaining chlorine atoms.

Mild reaction conditions were sufficient to convert compounds of the formula $N_3P_3Cl_5(OR)$ derived from desoxoestrone, estrone and estradiol 3-methyl ether to the corresponding amino compound by reaction with methylamine. Reaction of the estrone derivative, $N_3P_3Cl_5OR$, with methylamine yielded a product in which the carbonyl group at the 17-position had been converted to a methylimino residue. Treatment of this compound with water regenerated the carbonyl group without modifying the remainder of the molecule.

The facile replacement of all the chlorine atoms in $N_3P_3Cl_5(OR)$ by methylamino groups suggests that similar reactions with the analogous high polymers are feasible, as long as no more than one steroidal residue is present for every three repeating units. Compounds of the formula $N_3P_3Cl_5(OR)$ also undergo halogen replacement by ammonia, but the reaction products, $N_3P_3Cl_5(OR)$ degrade rapidly by hydrolysis in aqueous media.

Preferred compounds of the invention are those of the formula $P_3N_3(NHR_2)_5(OR_1)$, as above, wherein (a) $R_2$ is methyl;

(b) $R_1$ is

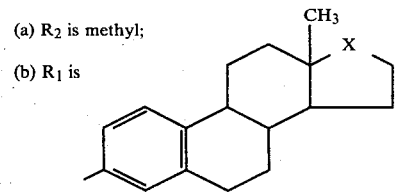

and X is C=O or $CH_2$, including (a); and (c) $R_1$ is

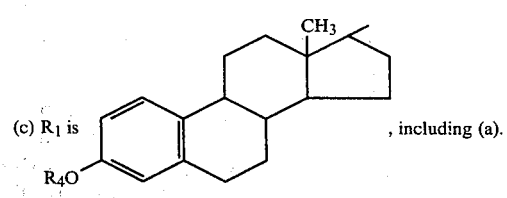

, including (a).

Steroid-substituted cyclic phosphazenes $N_3P_3Cl_5(OR)$ and $N_3P_3(NHCH_3)_5(OR)$ were characterized by $^{31}P$ nmr spectroscopy, and by infrared and ultraviolet spectroscopy and, in some cases by elemental microanalyses.

The mass spectrometric data were consistent with the expected elemental compositions of structures in which the OR groups were derived from desoxoestrone, estrone and estradiol 3-methyl ether. Strong parent peaks were found in each case. The typical high mass fragmentation patterns showed the successive loss of from one to three chloro- or methylamino groups to form fragments of the type $[N_3P_3-(OR)Cl_{5-x}]$·+ or $[N_3P_3(OR)(NHCH_3)_{5-x}]$·+ (where $x=1-3$). For the species of type $N_3P_3(NHMe)_5(OR)$ the fragmentation patterns also showed a successive loss of methyl groups.

The survival of the phosphazene ring was confirmed by the infrared P-N stretching frequencies in the 1175-1216 cm$^{-1}$ region. No significant differences could be discerned between the P-N absorption frequencies of the various species of general formula $N_3P_3(NHMe)_5(OR)$ ($\approx$1195 cm$^{-1}$). Infrared spectroscopy was used to identify the 17-methylimino residue of the side group derived from estrone and the subsequent hydrolysis of this unit back to the carbonyl function.

Because the cyclophosphazene ring has no significant ultraviolet absorption at wavelengths longer than 220 nm, substitution of chlorine by desoxestrone and estrone could be monitored by ultraviolet spectroscopy. The attachment of residues from the foregoing steroids to the phosphazene ring of $N_3P_3Cl_5(OR)$ or $N_3P_3(NHMe)_5(OR)$ resulted in a hypsochromic shift from 290 nm in the free steroid to 275.5 nm (in tetrahydrofuran). In contrast, no ultraviolet spectral shift took place when estradiol 3-methyl ether was attached to the phosphazene ring.

The $^{31}P$ nmr spectra of $N_3P_3Cl_5(OR)$ were interpreted as $AB_2$ spin systems, comparable to those of $N_3P_3Cl_5(OCH_2CF_3)$ or $N_3P_3Cl_5(OC_6H_5)$, J. L. Schmutz et al, *Inorg. Chem.*, vol. 14, 2433 (1975) and D. Dell et al, *J.Chem.Soc.*, 4070 (1965). The spectra of $N_3P_3(NHMe)_5(OR)$ were comparable to the $AB_3$ pattern of $N_3P_3(NHCH_3)_5(OCH_2CF_3)$. As is the case for other $AB_2$ spin systems, the chemical shifts and coupling constants for these compounds were both solvent- and concentration-dependent.

$^{13}C$ nmr spectra confirmed the retention of the steroidal framework after the linkage and cosubstitution reactions. Although the $^{13}C$ nmr spectra were insufficiently resolved to permit the indentification of every carbon nucleus in the steroid structure for compounds with the formula $N_3P_3(OR)Cl_5$, and $N_3P_3(OR)(NHMe)_5$, where HOR is desoxoestrone, estrone or estradiol 3-methyl ether, no change in the absorbances of the aromatic nuclei for estradiol 3-methyl ether occurred as a result of the interaction with sodium hydride or with $(NPCl_2)_3$.

These data indicate that no major side reactions involving the ether function at the 3-position of estradiol 3-methyl ether had occurred. In the case of estradiol 3-methyl ether, only a slight change in the relative intensity and no change in the chemical shift at 82 ppm was observed for the $^{13}C$ nuclei of desoxoestrone following reaction of the sodium salt thereof with $(NPCl_2)_3$. $^{13}C$ Nmr spectroscopy and mass spectrometry were also used to confirm the identify of the unreacted steroids isolated from the reaction products to confirm the absence of side reactions.

Products of the formulae $N_3P_3Cl_5OR$ and $N_3P_3(NHMe)_5(OR)$ were soluble in a variety of organic media, e.g., $C_1-C_4$ alkanols, acetones, etc. A compound of the structure $N_3P_3(NHMe)_5(OR)$ derived from estrone was soluble in water. This result suggests that water-soluble high polymeric analogues would require the presence of fewer than one steroidal residue per three repeating units, except when residues derived from estrone were present. Derivatives of the formula $N_3P_3Cl_5(OR)$ were insoluble in water, but hydrolyzed in contact with atmospheric moisture or aqueous base. Compounds of the formula $N_3P_3(NHMe)_5(OR)$ appeared to be stable to water at 25° C.

Due to their hormonal activity, the compounds of this invention are useful as estrogenic and fertility regulating agents in human and veterinary medicine. They can be employed, for example, in enteral and parenteral therapy in substantially the same manner as the known compounds estradiol, estradiol 3-methyl ether or estrone.

The compounds of this invention can be employed in mixture with conventional excipients, i.e., pharmaceutically acceptable organic or inorganic carrier substances suitable for parenteral or entereal application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oil or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10–500 mg of a pharmaceutical carrier per unit dosage and the amount of active agent of the invention per unit dosage is about 1 to 5 mg.

It will be appreciated that the actual preferred amounts of active compounds used will vary according to the specific compound being utilized, the particular compositions formulated, the mode of application, and the particular situs and organism being treated. Optimal application rates for a given set of conditions can be ascertained by those skilled in the art using conventional dosage determination tests in view of the above guidelines.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following examples, the temperatures are set forth uncorrected in degrees Celsius; unless otherwise indicated, all parts and percentages are by weight. The values obtained in elemental analyses are within commonly accepted limits of error.

REAGENTS AND SOLVENTS

Anhydrous methylamine (Linde Air Products or Matheson) was used as received. Triethylamine (Eastman) was distilled from barium oxide before use. Benzene and heptane (Fisher) were heated under reflux and then distilled from calcium hydride before use. Tetrahydrofuran (Fisher) was treated with lithium-aluminum hydride or sodium/benzophenone. Sodium hydride (50% dispersion in oil, Alfa Chemical), was washed with freshly distilled heptane before use. Estradiol 3-methyl ether (Sigma), estrone-3-methyl ether (Sigma), mestranol (Sigma), and estrone (Sigma or Aldrich) were dried in vacuo for 8 hrs before use. Hexachlorocyclotriphosphazene (mp 112° C.) was obtained from a trimer-tetramer mixture (El Monte Chemical Corp. or Ethyl Corp.) by twice repeated vacuum sublimation (60° C., 0.5 torr), recrystallization twice from heptane and two subsequent sublimations.

INSTRUMENTATION $^1$H Decoupled, $^{31}$P nmr spectra were obtained at 40.5 Hz using a Jeol PS 100 spectrometer operated in the Fourier transform mode and interfaced with a Nicolet 1080 data processor. Ultraviolet spectra were obtained from Varian 634 or Cary 17 ultraviolet spectrophotometers. Infrared spectra were obtained with the use of Perkin Elmer model 267, 261 and 580 spectrophotometers. Mass spectra were obtained with the use of an AEI/MS 902 mass spectrometer set at an ionization potential of 20 e.v. Perfluorinated kerosene was used as an internal reference as needed.

Elemental analyses were performed by Galbraith Laboratories, Knoxville, Tennessee in samples previously dried in vacuo for 8 hrs at 40° C., or 80° C.

EXAMPLE 1

Preparation of Desoxoestrone

Estrone (2.0 g, 7.4 mmol), hydrazine hydrate (0.888 g, 0.018 mol), and one drop of glacial acetic acid were added to 10 ml of triethylene glycol. The resulting mixture was stirred and heated to 125° C. Water produced by the reaction and excess hydrazine were removed by distillation and were discarded. The reaction flask was corked following addition of sodium methoxide (1.5 g, 0.0273 mol) in 10 ml of triethylene glycol. The mixture was heated to 170° C. for 1 hr and then to 190°–200° C. After one hour at this temperature, the temperature was lowered to 175° C. and maintained at 179° C. for 24 hrs more. Nitrogen evolution was less vigorous at the lower temperature. The reaction mixture was poured into water acidified with acetic acid or a mineral acid such as hydrochloric, and the precipitate which formed was collected and washed with water. The water-insoluble crystals were taken up in diethyl ether and the solution was filtered. Evaporation of the solvent from the filtrate gave crystals, which were dried under vacuum for 8 hrs. After several recrystallizations from a dilute solution in ethanol and water, a white crystalline material, melting between 135°–136° C., was obtained in 60% yield. The mass spectrum showed a parent peak at 255 amu (calculated 255). An infrared spectrum showed no carbonyl absorbance. Ultraviolet absorbance maxima were found at 291 and 282 nm (in diethyl ether).

EXAMPLE 2

Reaction of $(NPCl_2)_3$ with the Sodium Salt of Desoxoestrone

A solution of desoxoestrone (0.3084 g, 1.20 mmol) in tetrahydrofuran (200 ml) was heated under reflux with an excess of sodium hydride for 3 hrs. The solution was filtered under a stream of nitrogen and the resulting filtrate was added during 5 min to a warm solution of $(NPCl_2)_3$ (0.5 g, 1.4 mmol) in tetrahydrofuran (100 ml). Residual sodium hydride was washed with tetrahydrofuran (150 ml) and was removed by filtration. Addition of this filtrate to the reaction mixture brought the reaction mixture to a total volume of 450 ml. The reaction mixture was stirred constantly and heated under reflux for 12 hrs, after which the reaction mixture was allowed to cool to room temperature and was stirred for 3 days more. Evaporation of the solvent yielded a pale yellow oil which was dissolved in benzene and filtered to remove residual salts. Evaporation of the benzene gave a colorless oil that was decanted from the unreacted $(NPCl_2)_3$ and desoxoestrone. Ultraviolet absorbance maxima for the oily product were detected at 277.2 and 269.6 nm (in diethyl ether). Infrared $P=N$ absorption appeared at 1200 cm$^{-1}$. A mass spectrum showed a parent peak at m/e=567 (theory=568). The yield (based on $^{31}P$ nmr spectroscopy of the crude reaction mixture) was ≃30%.

EXAMPLE 3

Reaction of $(NPCl_2)_3$ with the Sodium Salt of Dexosoestrone and Methylamine

Desoxoestrone (0.369 g, 1.43 mmol) was dissolved in tetrahydrofuran (50 ml) and was stirred with excess sodium hydride at 25° C. for 8 hrs. After two additional hours of heating under reflux, the suspension was filtered under a stream of nitrogen. The filtrate was added to a solution of $(NPCl_2)_3$ (0.5 g, 1.43 mmol) in tetrahydrofuran (25 ml). The residue of sodium hydride was washed with tetrahydrofuran (25 ml) and was removed by filtration. Addition of the washings to the reaction mixture brought the volume of the solution to 100 ml. The resulting mixture was heated under reflux for 24 hrs with constant stirring and was then cooled in an ice bath. Methylamine (100 ml) was condensed into the reaction mixture using a dry ice condenser. After 2 hrs, the mixture was allowed to warm gradually to room temperature, at which stirring was continued for 1.5 days. The reaction mixture was filtered. The filtrate was concentrated and diluted with acetone to yield a white precipitate which was soluble in tetrahydrofuran, benzene, and chloroform, but was insoluble in ethanol. A solution of the precipitate in benzene was filtered and concentrated. Addition of acetone to the concentrated filtrate precipitated a spectroscopically pure, white, semicrystalline solid that melted at 105° C. The sample was redissolved in a minimum amount of tetrahydrofuran and a solid was precipitated by the addition of ethanol. The precipitate was filtered off and dried in air to give a white solid that melted at 142° C. The yield was approximately 30%. An ultraviolet spectrum of the product showed absorbance maxima at 275.5, 267.8, and 209 nm (in tetrahydrofuran). An infrared $P=N$ stretching peak was detected at 1190 cm$^{-1}$. A mass spectrum showed a parent peak at m/e=540 (theory=540).

EXAMPLE 4

Reaction of $(NPCl_2)_3$ with the Sodium Salt of Estrone and Methylamine

A solution of estrone (3 g, 0.0111 mol) in anhydrous tetrahydrofuran (100 ml) was stirred with excess sodium hydride at room temperature (27° C.) for 2 hrs. The suspension was filtered under a stream of nitrogen. The resulting filtrate was added to a stirred solution of $(NPCl_2)_3$ (5.1321 g, 0.01475 mol) in tetrahydrofuran (25 ml). Twelve hours later, methylamine (300 ml) was condensed into the mixture using a dry ice condenser. The thus-obtained mixture was stirred for 2 days, after which solvent and unreacted methylamine were allowed to evaporate and the residue was dissolved in benzene. Following filtration and evaporation of the benzene, the solid residue obtained was identified as a compound wherein OR is the methylimino derivative of estrone bonded to to the phosphazene ring through the 3-oxy group. (The methylimino group absorbed strongly in the infrared at 1670 cm$^{-1}$).

The methylimino-derivative was converted to the ketone by stirring the product obtained above in boiling water. The mixture was filtered. Water was evaporated from the filtrate using a rotary evaporator and steam water bath to yield a white residue which was soluble in ethanol and tetrahydrofuran. The product was precipitated with petroleum ether from a concentrated solution in tetrahydrofuran. The precipitate was isolated and redissolved in hot water. The solution was filtered and the water was evaporated from the filtrate. Quantitative conversion of the water-insoluble methylimine derivative to the water soluble ketone was demonstrated by infrared spectroscopy (strong carbonyl absorbance at 1740 cm$^{-1}$). Reprecipitation of the water-soluble residue from tetrahydrofuran by the addition of petroleum ether gave a white material that melted at 155° C. The overall yield was 30%. A crystal-crystal transition was detected at 137° C. A mass spectrum showed a parent ion at m/e=554 (theory=554). An infrared $P=N$ stretching peak was detected at 1190 cm$^{-1}$. Anal. Calcd. for $C_{23}H_{41}N_8O_2P_3$: C, 49.82; H, 7.40; N, 20.22; P, 16.79; Cl, 0; O, 5.78. Found: C, 49,99; H, 7.39; N, 19.94; P, 16.69; Cl, 0; O (by difference), 5.99.

EXAMPLE 5

Reaction of $(NPCl_2)_3$ with the Sodium Salt of Estradiol 3-Methylether and Methylamine.

A solution of estradiol 3-methylether (2.0056 g, 7.17 mmol) in anhydrous tetrahydrofuran (150 ml) was heated under reflux with excess sodium hydride for 5 hrs. The suspension was filtered under a stream of nitrogen. The filtrate was added to a solution of $(NPCl_2)_3$ (3.69 g, 0.106 mol) in tetrahydrofuran (100 ml). After the mixture had been stirred for 12 hrs at 27° C., the solvent was removed. The residue was dissolved in benzene and filtered. Evaporation of the benzene from the filtrate left an oily residue which was washed with petroleum ether to give a mixture of $(NPCl_2)_2NPClOR$ and $(NPCl_2)_3$ (15% conversion by $^{31}P$ nmr spectroscopy). A mass spectrum of the impure oil showed a peak at m/e=597 (theory=598). The conversion to IV as determined by $^{31}P$ nmr spectroscopy was 15%. The mixture was dissolved in anhydrous tetrahydrofuran (50 mL), and methylamine (300 mL) was added to the residue.

The resultant mixture was filtered. Benzene was evaporated from the filtrate by means of a rotary evaporator. Unreacted steroid was removed by washing the residue with a small amount of ethanol (100%) to yield an ethanol-insoluble solid or oil. The ethanolic layer was removed and discarded. Petroleum ether was added to the residue to yield a white precipitate, which was redissolved in benzene and filtered. The solution was concentrated. The product was isolated by reprecipitation from benzene by the addition of petroleum ether, washing with ethanol, reprecipitation from benzene-petroleum ether and dried in vacuum (0.5 torr) for 8 hrs at 80° C. The overall yield was 12.5% (m.p. 152°–154° C.). A mass spectrum showed a parent peak at m/e=570 (theory=570). An infrared P=N stretching peak was evident at 1195 cm$^{-1}$. Anal. Calcd. for $C_{24}H_{45}N_8O_2P_3$: C, 50.53; H, 7.89; N, 19.65; P, 16.32; Cl, 0; O, 5.61. Found: C, 50.53; H, 8.03; N, 19.52; P, 16.30; Cl, 0; O (by difference), 5.63.

EXAMPLE 6

Reaction of $(NPCl_2)_3$ with Cholesterol

Cholesterol (2.1105 g, 0.00546 mol) was dissolved in tetrahydrofuran (100 ml) was heated under reflux under a stream of nitrogen for 5 hrs with an excess of sodium hydride suspended therein. The suspension was filtered. The filtrate was added dropwise to a solution of $(NPCl_2)_3$ (1.9 g, 0.00546 mol) in tetrahydrofuran (100 ml). The mixture was stirred at 27° C. for 12 hrs. A concentrate of the pale-yellow turbid reaction mixture gave a $^{31}P$ nmr spectrum which suggested that 23% of the $(NPCl_2)_3$ had reacted, but the spectrum was inconsistent with the structure of a steroid-phosphazene ester (HOR=cholesterol) was interpreted as an $AB_2$ spin pattern compatible with the structure, $[N_3P_3(OH)Cl_5]$. Unreacted cholestrol (1.5 g, mp 143° C.) was precipitated by addition of pentane thereto. A mass spectrum of a fraction of the heptane-soluble residue, isolated by chromatography with silica gel and hexane, showed a parent ion at m/e=369 which was the ion from 3,5-cholestadiene (theory=368). This fraction had a melting point range from 78°–80° C. and an ultraviolet absorbance maximum at 234 nm (in hexane); 3,5-cholestadiene melts at 80° C. and has an absorbance maximum at 234 nm in cyclohexane. Less than a 5% yield of the anticipated product was detected by $^{31}P$ spectroscopy ($v_A$=14.6 ppm, $v_B$=22.6 ppm, and $J_{AB}$=64.2 Hz). $(NPCl_2)_3$ was identified from the mass spectral $Cl_6$-isotope pattern found at 345 a.u.

EXAMPLE 7

Interaction of Pregnenolone with $(NPCl_2)_3$

Pregnenolone (5 g, 1.58 mmol) was heated under reflux for 4 hours with sodium hydride (5 g, 20.8 mmol) in tetrahydrofuran. The mixture was filtered at 25° C. The product obtained following treatment with methyl iodide showed clear infrared spectral evidence of the presence of methoxy groups at the 3-position and at the 17-position for an ether from a C(OH)CH$_3$ unit by keto-enol tautomerism. Therefore, both the 3- and 17-positions of pregnenolone are reactive toward sodium hydride.

A similar mixture obtained as above was added dropwise over 1 hr to a rapidly-stirred solution of $(NPCl_2)_3$ (6 g, 1.72 mmol) at 0° C. in tetrahydrofuran (150 ml). The mixture was then stirred for 10 hrs at 25° C. An excess of liquid methylamine was condensed into the mixture by means of a Dry Ice condenser. The mixture was stirred at 0° C., for 1 hr and then at 25° C. for 24 hrs. Removal of the tetrahydrofuran was followed by dissolution in benzene, filtration, evaporation of the solvent, extraction with ethanol, and extraction with petroleum ether. The extent gave a 2% yield of a product (mp 82°–84° C.) that showed infrared and $^{31}P$ nmr spectra compatible with the expected structure. The product could not be separated sufficiently well from $[NP(NHCH_3)_2]_3$ impurity to yield a satisfactory microanalysis. Evidence was also obtained that the methylimino derivative was formed initially at the 20-position.

$^{31}P$ nmr data for the products of Examples 1–6 are given below in Table 1:

TABLE 1

| $^{31}P$ nmr Chemical Shifts and Coupling Constants[a,b] | | | | | |
|---|---|---|---|---|---|
| Compound | $V_A$ | $V_B$ | $V_{AB}$ | $J_{AB}$ | $J_{AB}/\Delta V$ |
| | Control Compounds | | | | |
| $N_3P_3Cl_5(OC_6H_5)$[c] | 9.91 | 19.9 | 9.95 | 1.55 | 0.155 |
| $N_3P_3Cl_5(OCH_2CF_3)$[g] | 14.1 | 20.4 | 6.24 | 1.65 | 0.264 |
| $(NPCl_2)_3$[c] | 20.0 | 20.0 | 0 | 0 | ∞ |
| $N_3P_3Cl_5(NMe_2)$[h] | 23.0 | 21.0 | 2 | 1.24 | 0.62 |
| $N_3P_3Cl_5(OH)$ | −4.54 | 16.8 | | 1.15 | |
| $[NP(NHCH_3)_2]_3$ | 23.0 | 23.0 | 0 | 0 | ∞ |
| $N_3P_3(NHCH_3)_5$ $(OCH_2CF_3)$ | 23.2 | 21.2 | 2.05 | 1.24 | 0.604 |
| HOR | $N_3P_3Cl_5(OR)$ | | | | |
| desoxoestrone[d] | 11.7 | 21.7 | 10.1 | 1.55 | 0.154 |
| estrone[c] | 11.9 | 21.9 | 10.1 | 1.51 | 0.150 |
| estradiol 3-methyl ether[c] | 14.2 | 21.5 | 7.35 | 1.55 | 0.213 |
| HOR | $N_3P_3(NHCH_3)_5(OR)$[f] | | | | |
| desoxoestrone[c] | 21.6 | 20.6 19.1 | ≈1.00 | 1.32 | 1.32 |
| estrone[c] | 20.7 | 20.1 | ≈1.0 | ≈1.3 | 1.3 |
| estradiol 3-methyl ether[c] | 18.7 | 18.7 | 0 | 0 | ∞ |
| estradiol 3-methyl ether[d] | 21.4 | 21.4 | 0 | 0 | ∞ |

[a] All the samples were proton decoupled and were interpreted as $AB_2$ spin systems. Assignments were approximated using the program NMR, LMA written by W.F. Slivinski, D.L. Doerfler, and K.J. Johnson which was used to simulate the $AB_2$ nmr spectrum.
[b] $V_{AB}$ + $V_A$ − $V_B$ (ppm) where $V_A$ = line 3 and $V_B$ = $\frac{\text{line 5 + line 7}}{2}$
$J_{AB} = \frac{1}{2}[(V_8 - V_6) + (V_4 - V_1)]$.
[c] The sample was dissolved in tetrahydrofuran.
[d] The sample was dissolved in $D_6$-benzene and no $D_2O$ capillary lock was employed.
[e] The spectrum was obtained as a neat liquid.
[f] These spectra were not sufficiently well-resolved to allow exact assignments to be made.
[g] J.L. Schmutz et al, Inorg. Chem., vol. 14, 2433 (1975)
[h] F. Heatly et al, J. Chem. Soc. (A) 1152 (1966).

EXAMPLE 8

A composition of the formula $N_3P_3(NHMe)_5(OR)$ in which OR is derived from estrone (Example 4) is finely powdered and mixed with 99% by weight of powdered lactose. Weighed portions of 150 mg are sealed in aluminum envelopes lined with vinylidene chloridevinyl acetate copolymer and sealed against moisture to prevent caking.

EXAMPLE 9

Dosage units prepared as in Example 8, containing 1% by weight of steroidal cyclotriphosphazene and 99% by weight of lactose and weighing 250 mg, were filled into hard gelatin capsules of an appropriate size.

An alternative formulation is:
2% estrone-cyclotriphosphazene of Example 4
95% corn starch 3% anhydrous silica

EXAMPLE 10

A composition of the formula $N_3P_3(NHMe)_5(OR)$, in which OR is derived from estradiol 3-methyl ether as in Example 5, is finely powered and blended with 90% by weight or powdered amylose. Weighed portions of 25 mg. are prepared as in Example 8.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A compound of the formula

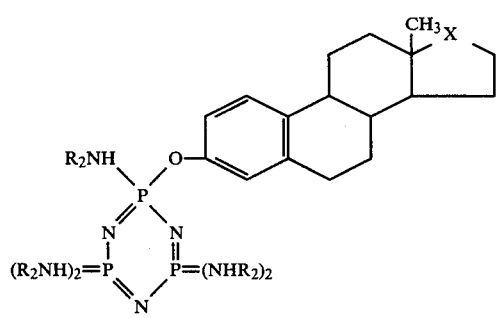

wherein

R$_2$ is alkyl of 1–4 carbon atoms and

X is CH$_2$ or C=O.

2. A compound of claim 1, wherein R$_2$ is methyl.

3.

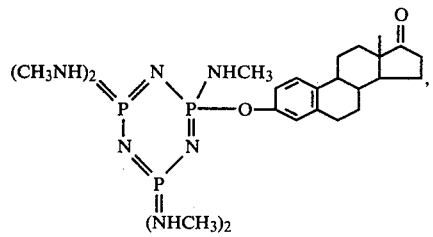

a compound of claim 1.

4.

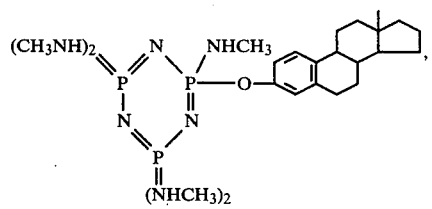

a compound of claim 1.

5. A compound of the formula

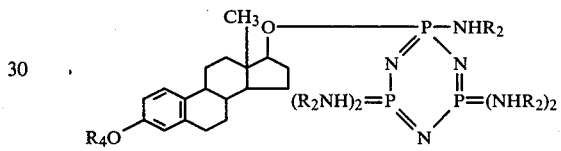

wherein

R$_2$ is alkyl of 1–4 carbon atoms and

R$_4$ is alkyl of 1–4 carbon atoms.

6.

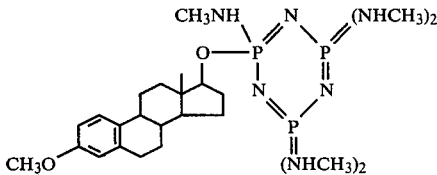

a compound of claim 5.

7. A compound of claim 5, wherein R$_2$ is methyl.

8. A slow release steroidal medicament, comprising a compound of claim 1, in admixture with a pharmaceutically acceptable carrier.

9. A slow release steroidal medicament, comprising a compound of claim 5, in admixture with a pharaceutically acceptable carrier.

* * * * *